United States Patent
Lee et al.

(10) Patent No.: US 9,398,934 B2
(45) Date of Patent: Jul. 26, 2016

(54) SURGICAL TOOL, SURGICAL ROBOT HAVING THE SAME, AND REMOTE CONTROL ROBOT SYSTEM

(71) Applicant: SAMSUNG ELECTRONICS CO., LTD., Suwon-si, Gyeonggi-do (KR)

(72) Inventors: Hyung Kew Lee, Gunpo-si (KR); Soo Chul Lim, Seoul (KR); Joon Ah Park, Hwasung-si (KR); Bho Ram Lee, Sungnam-si (KR); Seung Ju Han, Seoul (KR); Hyun Jeong Lee, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 519 days.

(21) Appl. No.: 13/783,889

(22) Filed: Mar. 4, 2013

(65) Prior Publication Data
US 2014/0012286 A1 Jan. 9, 2014

(30) Foreign Application Priority Data
Jul. 5, 2012 (KR) ........................ 10-2012-0073343

(51) Int. Cl.
*A61B 17/29* (2006.01)
*A61B 19/00* (2006.01)

(52) U.S. Cl.
CPC ..... *A61B 19/2203* (2013.01); *A61B 2017/2926* (2013.01); *A61B 2017/2936* (2013.01)

(58) Field of Classification Search
CPC .... A61B 17/29; A61B 17/28; A61B 17/2804; A61B 2017/2926; A61B 34/37; A61B 34/74; A61B 2562/0247; A61B 2562/0266
See application file for complete search history.

(56) References Cited

U.S. PATENT DOCUMENTS

| 5,772,597 | A | 6/1998 | Goldberger et al. | |
|---|---|---|---|---|
| 8,083,120 | B2 | 12/2011 | Shelton, IV et al. | |
| 2007/0074584 | A1* | 4/2007 | Talarico et al. | 73/856 |
| 2010/0094271 | A1* | 4/2010 | Ward et al. | 606/33 |
| 2011/0251605 | A1 | 10/2011 | Hoarau et al. | |

FOREIGN PATENT DOCUMENTS

| JP | 6-269391 | 9/1994 |
|---|---|---|
| JP | 9-98978 | 4/1997 |
| JP | 2010-69304 | 4/2010 |

* cited by examiner

*Primary Examiner* — Katherine M Shi
*Assistant Examiner* — Michael Mendoza
(74) *Attorney, Agent, or Firm* — NSIP Law

(57) ABSTRACT

A remote control robot system includes a surgical robot having a surgical tool which is used to perform minimally invasive surgery. The surgical tool includes a detection member having a plurality of detection parts, a support member, and an optical fiber disposed between the detection member and support member. A magnitude of force and a distribution of the force may be measured by individually disposing a plurality of optical fiber bragg gratings (FBGs) below the plurality of detection parts, respectively. Accordingly, the surgical robot or the remote control robot system may provide a more precise control function and a hand-touch diagnosis function.

19 Claims, 6 Drawing Sheets

SURGICAL TOOL, SURGICAL ROBOT HAVING THE SAME, AND REMOTE CONTROL ROBOT SYSTEM

CROSS-REFERENCE TO RELATED APPLICATIONS

This application claims the priority benefit of Korean Patent Application No. 10-2012-0073343, filed on Jul. 5, 2012, in the Korean Intellectual Property Office, the disclosure of which is incorporated herein by reference.

BACKGROUND

1. Field

One or more embodiments of the following description relate to a surgical tool, a surgical robot having the same, and a remote control robot system.

2. Description of the Related Art

Medically, surgery refers to medical treatment in which a subject's skin, mucous membrane, or other tissues are cut or opened using a surgical tool so that a medical professional (e.g., a surgeon or doctor) may repair, remove, or replace a diseased or damaged part.

Minimally invasive surgery (MIS) refers to a type of a surgical operation to minimize a burden borne by a patient. For example, MIS minimizes a size or area of tissue which is opened during surgery, which may result in a shorter hospital stay or the surgery may be performed in an outpatient facility. MIS refers to a type of surgery in which a small insertion hole is punctured instead of cutting the skin. A surgical tool, such as an endoscope, a laparoscope, a microscope for microsurgery, and the like, for example, may be inserted through the insertion hole to perform the surgery within a body.

The above MIS may be performed manually by a medical professional (e.g., a surgeon or doctor), and may also be performed in such a manner that the medical professional may elaborately control a surgical tool through a surgical robot instead of directly controlling the surgical tool. The surgical robot may adjust a level of the medical professional's motion that is transferred to the surgical tool. Trembling of the medical professional's hand may be prevented on the way and thus, the surgical robot may be employed for surgery that requires minute and precise control of a surgical instrument.

SUMMARY

The foregoing and/or other aspects are achieved by providing a surgical tool, including: a support member to be guided to a surgery portion; a plurality of detection parts provided on the support member and of which a front surface contacts with a surgery portion or a surgical instrument; and a detection sensor disposed between the support member and each of the plurality of detection parts to measure force transferred to each of the plurality of detection parts.

The detection sensor may include an optical fiber disposed along a rear surface of each of the plurality of detection parts, and the optical fiber may be disposed within a groove formed in the support member.

The optical fiber disposed on a bottom surface of each of the plurality of detection parts may be provided with an optical fiber bragg grating (FBG). Due to force transferred from each of the plurality of detection parts, the FBG may receive a tensile force from a lengthwise direction to measure force applied to each of the plurality of detection parts.

The plurality of detection parts may be separated from each other to be mutually independently movable upward and downward, and a biocompatible elastic material may be provided between the respective detection parts or between each of the plurality of detection parts and the support member.

A convex protruding portion may be formed on a rear surface of each of the plurality of detection parts, and a concave groove portion in a shape corresponding to the protruding portion may be formed in the support member. The detection sensor may include an optical fiber disposed along the rear surface of each of the plurality of detection parts, and an optical fiber positioned on a center of a bottom surface of the protruding portion may be provided with an FBG. Due to force transferred from each of the plurality of detection parts, the FBG may receive a tensile force from a lengthwise direction to measure force applied to each of the plurality of detection parts. A single FBG may be provided on the rear surface of each of the plurality of detection parts, and the magnitude or distribution of the force applied to each of the plurality of detection parts may be measured by measuring a change in a wavelength of light reflected from the FBG.

The foregoing and/or other aspects are achieved by providing a surgical robot, including: a master input unit having a controller; a robot arm to operate according to a control of the master input unit; and a surgical tool including at least one grasper connected to a front end of the robot arm. Each of the at least one grasper that is provided with a pair of grips capable of being opened and closed based on a joint, may include: a support member included in each of the pair of grips; a detection member provided on the support member and of which front surface contacts with a surgery portion or a surgical instrument; and an optical fiber disposed between the support member and the detection member to measure force transferred to the detection member. A plurality of FBGs may be formed on the optical fiber disposed on a bottom surface of the detection member, and due to force transferred from the detection member, each of the FBGs may receive a tensile force from a lengthwise direction to measure force applied to the detection member.

The detection member may be divided into a plurality of detections parts, and the plurality of detection parts may be separated from each other to be mutually independently movable upward and downward.

The plurality of detection parts may be disposed along parallel rows, and a plurality of optical fibers may be disposed in parallel to locate the FBGs on the rear surface of each of the plurality of detection parts.

Alternatively, the plurality of detection parts may be disposed along parallel rows, and a single optical fiber may be disposed in a zigzagged form or pattern to locate the FBGs on the rear surface of each of the plurality of detection parts.

A convex protruding portion may be formed on a rear surface of the detection member, a concave groove portion in a shape corresponding to the protruding portion may be formed in the support member, and the FBG may be disposed on a center of the protruding portion.

A display may be provided to the master input unit, and distribution or magnitude of the force measured by the plurality of FBGs may be visually displayed on the display.

The force measured by the plurality of FBGs may be transferred by the controller of the master input unit to provide appropriate feedback to an operator.

The foregoing and/or other aspects are achieved by providing a remote control robot system, including: a master input unit having a controller; and a slave robot to operate according to a remote control of the master input unit, the slave robot having a robot arm with a surgical tool including a grip on a front end of the robot arm. The grip may include a support member connected to the front end of the robot arm; a plurality of detection parts provided on the support member to contact with a target object gripped; and an optical fiber disposed between the support member and each of the plurality of detection parts to locate a single FBG on a rear surface of each of the plurality of detection parts. A wavelength signal of light reflected from each of the FBGs may be transferred to the master input unit and magnitude or distribution of force applied to each of the plurality of detection parts may be measured based on a change in a wavelength.

The surgical tool may include a grasper to hold an object, having a pair of grips to perform an opening and closing operation, and at least one of the grips includes the support member and the plurality of detection parts. The optical fiber may be disposed in a groove, the groove being formed in a lengthwise direction on a front side of the support member facing the detection member. Each of the plurality of detection parts may include a front side to contact the target object and a rear side facing the support member, a portion of the rear surface protruding toward the support member having a convex shape, and the support member may include a plurality of concave groove portions, each corresponding to the convex protruding portion of the respective detection parts. Each of the respective FBGs may be disposed in a space between the convex protruding portion and the concave groove portion. Each of the respective FBGs may be disposed in the space at a position corresponding to a center of the convex protruding portion. A biocompatible elastic material may be disposed between each of the plurality of detection parts and the support member.

Additional aspects of embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of embodiments, taken in conjunction with the accompanying drawings of which.

DETAILED DESCRIPTION

Figure 1:
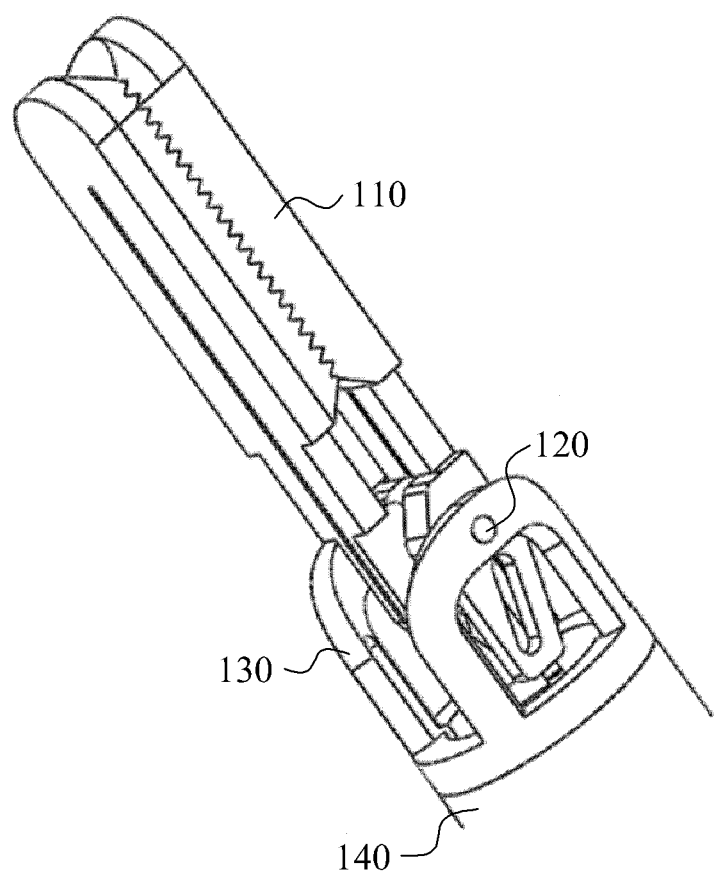
FIG. 1 illustrates a perspective view of a surgical tool according to an embodiment.

Reference will now be made in detail to embodiments, examples of which are illustrated in the accompanying drawings, wherein like reference numerals refer to like elements throughout. Embodiments are described below to explain the present disclosure by referring to the figures.

Terminologies used herein are defined to appropriately describe the embodiments and thus, may be changed depending on a user, the intent of an operator, a custom, and the like. Accordingly, the terminologies may be defined based on the following overall disclosure.

A surgical tool according to an embodiment may include a support member, a plurality of detection parts, and a detection sensor to measure force transferred to each of the plurality of detection parts.

The surgical tool may be mounted to a front end of a robot arm that is driven through a remote control and thus, may be employed for invasive surgery and the like. Here, it is noted that the robot arm and surgical tool may be positioned in a surgery site as needed to perform a desired operation. The robot arm and surgical tool may be integrated or separately disposed (e.g., the surgical tool may be detachable from the robot arm). Further, the robot arm may be portable, may be fixed, or may be detachably disposed to a site (e.g., the railing of an operating table, or other object).

Figure 2A:
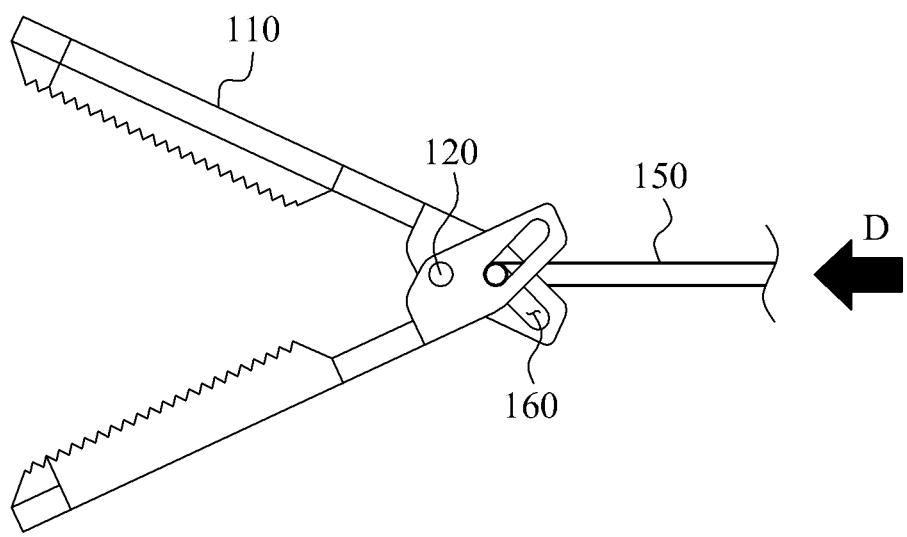
FIGS. 2A and 2B illustrate side views of an operation of opening and closing a surgical tool according to an embodiment.
Figure 2B:
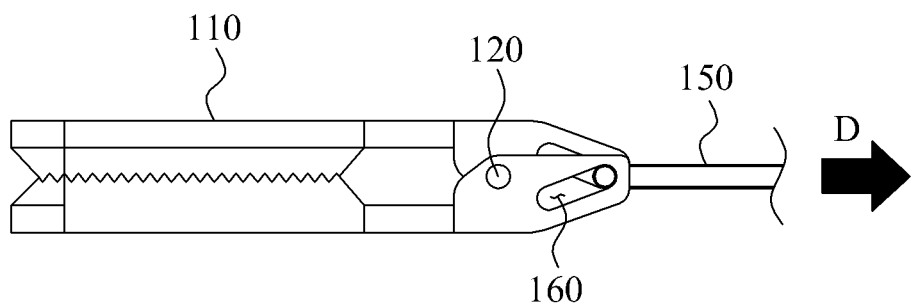

FIG. 1 illustrates a perspective view of a surgical tool 100 according to an embodiment, and FIGS. 2A and 2B illustrate side views of an operation of opening and closing the surgical tool 100 according to an embodiment.

The surgical tool 100 may be configured so that an instrument having various shapes based on a purpose or desired use, may be movable based on a joint with multiple degrees of freedom. The present embodiment will be described by employing, as an example, a grasper that is one of the most widely used instruments. The grasper refers to an instrument that is employed to tightly hold a surgical instrument or object such as tissue, thread, and the like during an operation. However, other surgical instruments may be utilized, including for example, such as scissors, a needle holder, a micro-dissector, a staple applier, a tacker, a suction irrigation tool, a clip applier, a cutting blade, an irrigator, a catheter, and/or a suction orifice.

Referring to FIG. 1 and FIGS. 2A and 2B, the surgical tool 100 may include a grip 110, a rotating axis 120, a part for the rotating axis 130, a pipe 140, a driving shaft 150, and a driving slit 160.

The grip 110 according to the present embodiment may be provided to perform an opening and closing operation based on the rotating axis 120. For example, a pair of grips 110 are configured to be opened and closed based on the rotating axis 120 and thus, may grip an object.

The grip 110 may measure a distribution or magnitude of force that is transferred from an object, for example, a tissue, a surgical instrument, and the like, gripped by the opening and closing operation, which will be further described in detail.

FIG. 2A illustrates a state in which a pair of grips 110 are opened, and FIG. 2B illustrates a state in which a pair of grips 110 are closed.

As shown in FIG. 2A, when an end of the driving shaft 150 moves forward within the driving slit 160 by a driving force D that faces a front direction, a pair of grips 110 may rotate based on the rotating axis 120 and be opened. That is, if a driving force D is applied in a direction towards the pair of grips 110, the end of the driving shaft 150 may move forward within the driving slit 160. A rivet may be disposed on the end of the driving shaft 150 as a pivot point such that the pair of grips 110 rotates to a full open position when the rivet moves fully forward to an end of the driving slit 160.

On the contrary, as shown in FIG. 2B, when the end of the driving shaft 150 moves backward within the driving slit 160 by a driving force D that faces a rear direction, a pair of grips 110 may rotate based on the rotating axis 120 and be closed.

That is, if a driving force D is applied in a direction away from the pair of grips 110, the end of the driving shaft 150 may move backward within the driving slit 160. An object, for example a rivet, may be disposed on the end of the driving shaft 150 as a pivot point such that the pair of grips 110 rotates to a full closed position when the rivet moves fully backward to the other end of the driving slit 160.

Even though the driving shaft 150 is described to move forward or backward as an example in FIGS. 2A and 2B, a method of driving a pair of grips 110 by pulling forward or backward a steel wire fixed to a pulley based on a rotating axis may be employed.

Through the above opening and closing operation of a pair of grips 110, an object may be stably and tightly gripped between a pair of grips 110.

Figure 3:
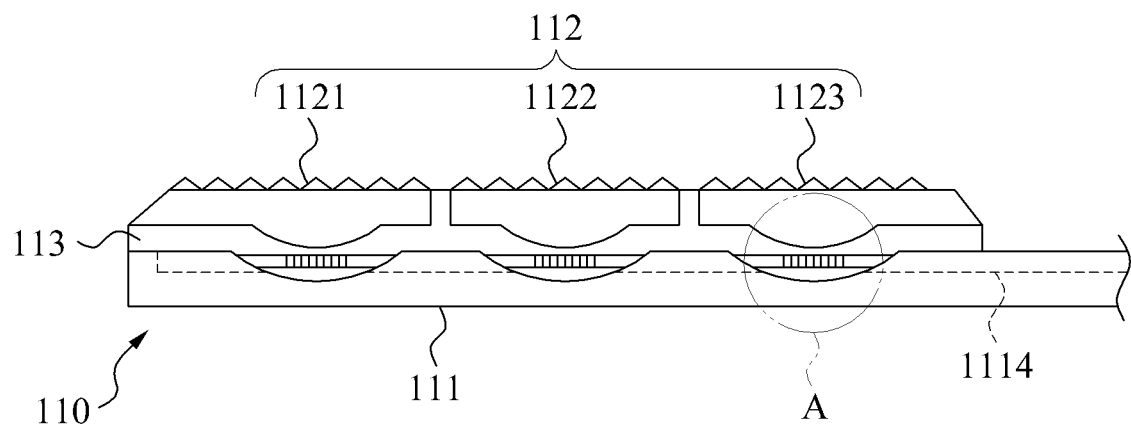
FIG. 3 illustrates a side configuration view of a surgical tool according to an embodiment.
Figure 4:
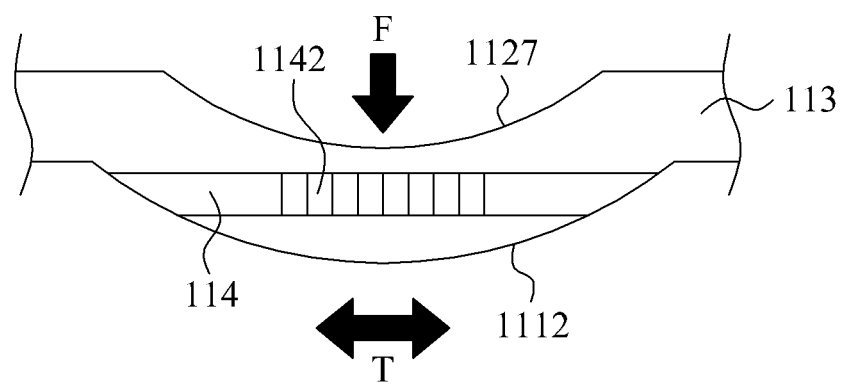
FIG. 4 illustrates an enlarged view of a portion A of FIG. 3.
Figure 5:
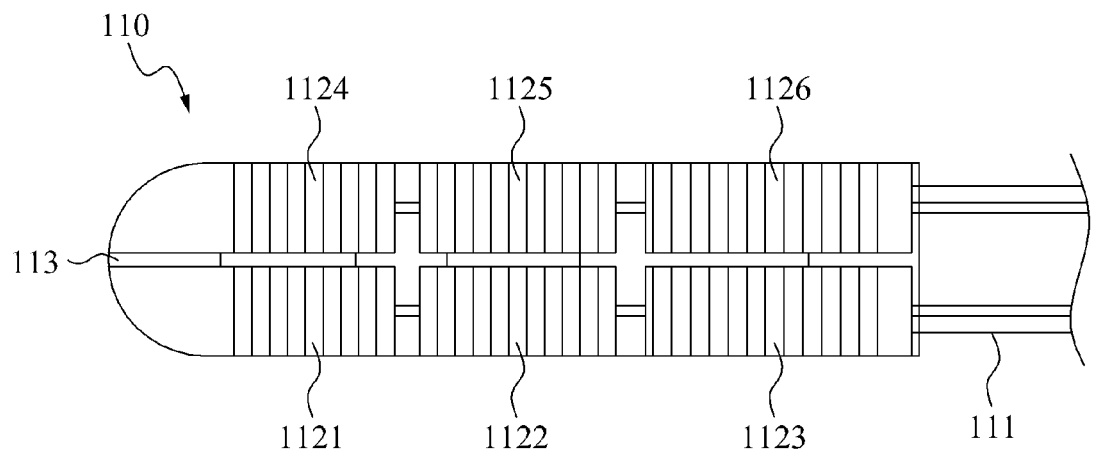
FIG. 5 illustrates a top view of a surgical tool according to an embodiment.
Figure 6:
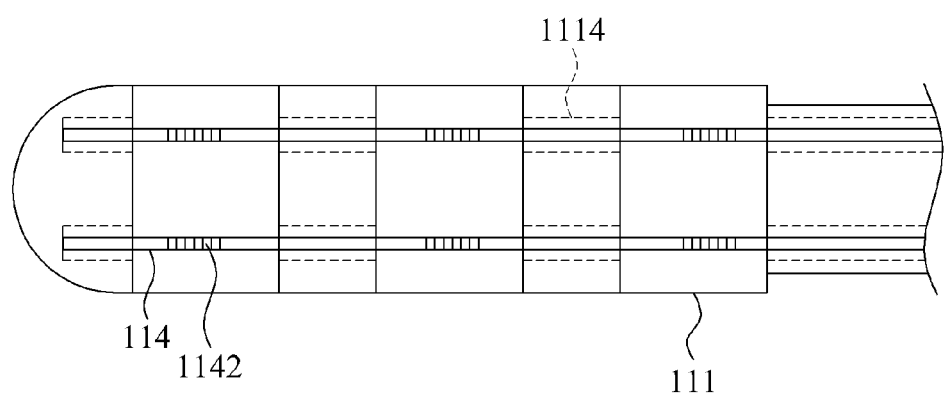
FIG. 6 illustrates a support member of a surgical tool according to an embodiment.
Figure 7:
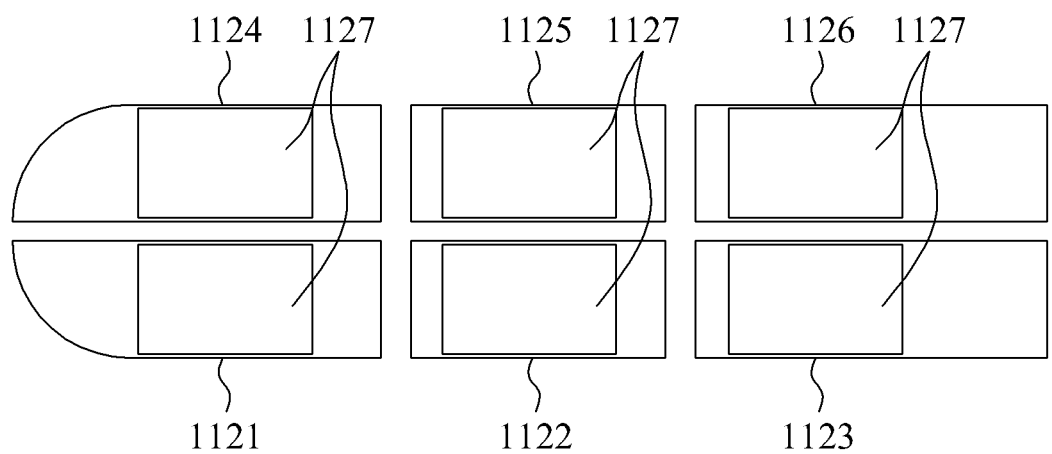
FIG. 7 illustrates a detection part of a surgical tool according to an embodiment.

FIG. 3 illustrates a side configuration view of the surgical tool 100 according to an embodiment, FIG. 4 illustrates an enlarged view of a portion A of FIG. 3, and FIG. 5 illustrates a top view of the surgical tool 100 according to an embodiment. FIG. 6 and FIG. 7 illustrate an exploded view of the surgical tool 100.

Referring to FIG. 3 through FIG. 5, the surgical tool 100 may include a support member 111 connected to a front end of a robot arm to be guided to a surgery portion or object, and a detection member 112 including a plurality of detection parts provided on the support member 111. The front surface of the detection member 112 contacts the surgery portion or a surgical instrument, and a detection sensor (e.g., optical fiber 114) disposed between the support member 111 and each of the plurality of detection parts measures a force transferred to each of the plurality of detection parts included in the detection member 112.

The rotating axis 120 and the driving slit 160 may be formed on one side of the support member 111. The support member 111 may perform an opening and closing operation about the rotating axis 120 along a forward and backward motion of the driving shaft 150.

The plurality of detection parts included in the detection member 112 may be disposed on the support member 111. For example, the plurality of detection parts included in the detection member 112 may be provided within (e.g., on an inner side of) the grip 110, and may be provided on each of a pair of grips 110, or may be provided on only one of the pair of grips 110.

The plurality of detection parts included in the detection member 112 may be disposed on an area of the support member 111 that is divided into a plurality of sections. For example, as shown in FIG. 3 and FIG. 5, a first detection part 1121, a second detection part 1122, and a third detection part 1123 may be disposed to be side by side along a front end of the grip 110. A fourth detection part 1124, a fifth detection part 1125, and a sixth detection part 1126 may also be disposed to be side by side along the front end of the grip 110 so as to constitute a second row of detection parts which may be in parallel with the first detection part 1121, the second detection part 1122, and the third detection part 1123, respectively. For example, as shown in FIG. 5, the first detection part 1121 is disposed directly opposite of the fourth detection part 1124. Even though six detection parts are described as an example in the present embodiment, it is only an example. For example, there may be more than or less than six detection parts. Further, a plurality of detection parts may be disposed to be in a single row, and may also be disposed to be in three or more rows. The number of detection parts and/or number of rows may be determined according to the size of the grip 110, or according to the size of the surgical tool in general, which may also be determined according to a desired operation of the surgical tool.

The first detection part 1121, the second detection part 1122, the third detection part 1123, the fourth detection part 1124, the fifth detection part 1125, and the sixth detection part 1126 (hereinafter, the first through sixth detection parts 1121 through 1126) may be separated from each other to be mutually independent, and may be vertically movable by a force applied on the front surface, without being affected by neighboring detection parts. For example, a force may be applied to detection part 1124 due to contact with an object, while the remaining detection parts are not affected or do not receive a force from the object.

A biocompatible elastic material 113 may be disposed between the first through sixth detection parts 1121 through 1126, so that the first through sixth detection parts 1121 through 1126 may smoothly move without being affected by neighboring detection parts. For example, as shown in FIG. 3, a space is formed between each of the detection parts 1121, 1122, and 1123 by using the biocompatible elastic material 113. Also, the biocompatible elastic material 113 may be disposed between the support member 111 and each of the first through sixth detection parts 1121 through 1126, so that the first through sixth detection parts 1121 through 1126 may smoothly move upward and downward.

The biocompatible elastic material 113 may be formed of a biocompatible rubber material, for example, silicon rubber.

A convex protruding portion 1127 shaped in a smoothly curved shape may be formed on a rear surface of the detection member 112. A concave groove portion 1112 in a shape corresponding to the protruding portion 1127 may be formed in the support member 111. That is, the protruding portion 1127 may be formed on a rear or lower surface of each of the first through sixth detection parts 1121 through 1126 included in the detection member 112. The groove portion 1112 may be concavely formed in the support member 111 at a position that faces the rear surface of each of the first through sixth detection parts 1121 through 1126 to pair the protruding portion 1127. For example, as shown in FIG. 4, the concave groove portion 1112 may be formed below the convex protruding portion 1127 and below an optical fiber 114.

A groove 1114 may be formed in the support member 111 along a lengthwise direction of the support member 111. The groove 1114 may be formed on a face of the support member 111 that faces the detection member 112. That is, an upper portion or upper surface of the support member 111 may refer to the portion or surface of the support member 111 which is closest to a detection part, relative to a lower portion or lower surface of the support member 111, and the groove 1114 may be disposed on an upper portion or upper surface of the support member 111.

The groove 1114 may be formed in the support member 111 to be in parallel with a line that connects centers of the first detection part 1121, the second detection part 1122, and the third detection part 1123, and may also be formed in the support member 111 to be in parallel with a line that connects centers of the fourth detection part 1124, the fifth detection part 1125, and the sixth detection part 1126.

The detection sensor may include an optical fiber 114 disposed along a rear surface of the detection member 112, and the optical fiber 114 may be disposed within the groove 1114. That is, a lower portion or lower surface of a detection part may refer to the portion or rear surface of the detection member 112 which is closest to the support member 111, relative to an upper portion or upper surface of the detection member 112, and the optical fiber 114 may be disposed on a lower portion or lower surface of the detection part.

For example, the optical fiber 114 may be disposed to be in parallel with the line that connects centers of the first detection part 1121, the second detection part 1122, and the third detection part 1123, and may also be disposed to be in parallel with the line that connects centers of the fourth detection part 1124, the fifth detection part 1125, and the sixth detection part 1126.

The optical fiber 114 may be disposed between the support member 111 and the detection member 112 and thus, may measure force transferred to each of the first through sixth detection parts 1121 through 1126 included in the detection member 112.

As shown in FIG. 4 and FIG. 6, the optical fiber 114 may include an optical fiber bragg grating (FBG) 1142.

The FBG 1142 may measure a physical change by generating a bragg grating that reflects a predetermined wavelength in the optical fiber 114 and by measuring a change in the reflected wavelength according to tension-compression or a change in temperature. In general, germanium (Ge) may be added to an optical fiber core in order to enhance a refractive index compared to cladding. A structural defect may occur while stably receiving the above germanium material in a silica glass. In this case, when emitting strong ultraviolet rays towards the optical fiber core, a binding structure of germanium may vary, and a refractive index of the optical fiber 114 may also vary. The FBG 1142 may periodically change a refractive index of the optical fiber core using the above phenomenon. The FBG 1142 may have a characteristic of reflecting only a wavelength that satisfies a bragg condition and transmitting a remaining wavelength as is. Thus, according to a characteristic of the FBG 1142, the FBG may reflect particular wavelengths of light and transmit all others. When an ambient temperature of the FBG 1142 changes or tension is applied to the FBG 1142, a refractive index or a length of the optical fiber 114 may vary and thus, a wavelength of light reflected may also vary. Accordingly, temperature, tension, pressure, bending, and the like may be detected by measuring a wavelength of light in the FBG 1142.

A plurality of FBGs 1142 may be formed in the optical fiber 114 that may be positioned below the first through sixth detection parts 1121 through 1126, respectively. Specifically, a single FBG 1142 may be disposed in a space between the protruding portion 1127 and the groove portion 1112 right below the protruding portion 1127 that is formed on the rear surface of each of the first through sixth detection parts 1121 through 1126.

The plurality of FBGs 1142 formed in the optical fiber 114 may be disposed right below the first through sixth detection parts 1121 through 1126 to receive a tensile force T due to a vertical force F that may be applied to the first through sixth detection parts 1121 through 1126, respectively.

As shown in FIG. 4, when the first through sixth detection parts 1121 through 1126 receive the vertical force F, the first through sixth detection parts 1121 through 1126 may apply a force to the plurality of FBGs 1142 by compressing the biocompatible elastic material 113. In this instance, a stress that is applied to a center and an edge of each of the FBGs 1142 may vary based on a shape of the protruding portion 1127 of each of the first through sixth detection parts 1121 through 1126 and the groove portion 1112 of the support member 111. Accordingly, the FBG 1142 may receive the tensile force T in a lengthwise direction and a wavelength of light reflected from the FBG 1142 may also vary.

By reading a change in the wavelength of light reflected from the FBG 1142, the vertical force F applied to each of the first through sixth detection parts 1121 through 1126 may be calculated. Since a single FBG 1142 is formed for each of the first through sixth detection parts 1121 through 1126, the magnitude and distribution of the vertical force F corresponding to the number of detection parts included in the detection member 112 may be measured.

FIG. 6 illustrates a top view of the support member 111 according to an embodiment, and FIG. 7 illustrates a plurality of detection parts included in the detection member 112 according to an embodiment. FIG. 6 and FIG. 7 illustrates a state before bonding the support member 111 and the detection member 112 using silicon rubber that may constitute the biocompatible elastic material 113.

Hereinafter, a manufacturing process of the surgical tool 100 will be described. Initially, the detection member 112 is disposed so that the protruding portion 1127 may face upward. The groove portion 1112 for detecting force and the groove 1114 for installing the optical fiber 114 are formed in the support member 111. The FBG 1142 may be disposed in a center of each groove portion 1112.

By fixing the support member 111 and the detection member 112 at a predetermined interval using a particularly prepared external frame and then injecting and hardening the biocompatible elastic material 113, for example, liquid silicon rubber between the support member 111 and the detection member 112, the surgical tool 110 may be manufactured. That is, a plurality of protruding portions 1127 may be spaced apart at fixed intervals in one or more rows of the detection member 112, and a plurality of groove portions 1112 may be spaced apart at corresponding fixed intervals in one or more rows of the support member 111, the protruding portions and groove portions being spaced apart in both lengthwise and widthwise directions.

As shown in FIG. 6 and FIG. 7, the surgical tool 100 may be configured so that two optical fibers 114 may be disposed to be in parallel. In this instance, three FBGs 1142 may be formed on each of the two optical fibers 114 and a single FBG 1142 may respectively be disposed below the protruding portion 1127 that is formed on each of the first through sixth detection parts 1121 through 1126.

Figure 8:
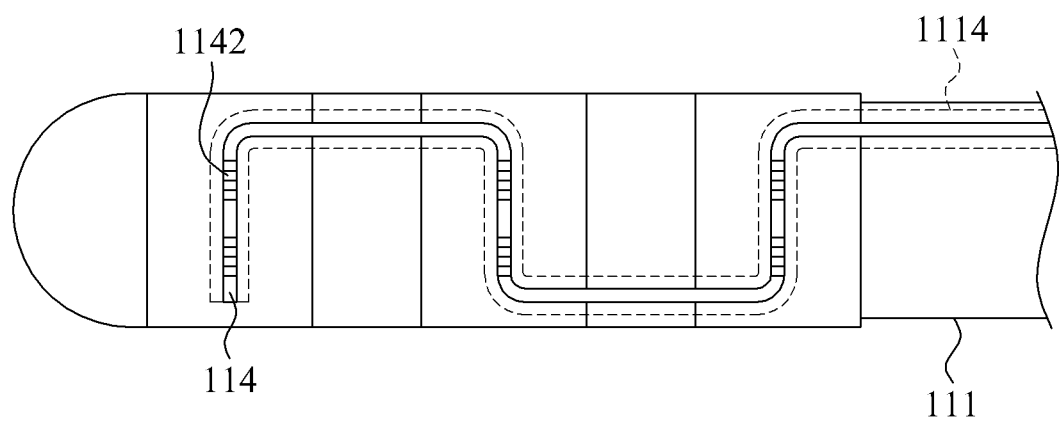
FIG. 8 illustrates a detection part of a surgical tool according to another embodiment.

FIG. 8 illustrates the detection part 111 according to another embodiment. As shown in FIG. 8, a single flexible optical fiber 114 may be disposed in a zigzagged form to pass below the first through sixth detection parts 1121 through 1126. In this instance, the groove 1114 of the support member 111 may be formed in a zigzagged form to pass below the first through sixth detection parts 1121 through 1126. In FIG. 8, it can be seen that the groove 1114 of the support member may first extend below the detection part corresponding to detection part 1126, then to detection part 1123, detection part 1122, detection part 1125, detection part 1124, and finally to detection part 1121.

When the optical fiber 114 is disposed in the zigzagged form, the FBG 1142 may be disposed below the protruding portion 1127 that is formed on each of the first through sixth detection parts 1121 through 1126. The disclosure is not limited to the zigzag form shown in FIG. 8, and may be shaped differently. For example, the groove 1114 of the support member may first extend below the detection part corresponding to detection part 1123, then to detection part 1126, detection part 1125, detection part 1122, detection part 1121, and finally to detection part 1124. Additionally, the groove 1114 of the support member may be substantially u-shaped to first extend below the detection part corresponding to detection part 1126, then to detection part 1125, detection part 1124, detection part 1121, detection part 1122, and finally to detection part 1123. Alternatively, the substantially u-shaped groove may first extend below detection part 1123. Other variations of the above are possible.

Figure 9:
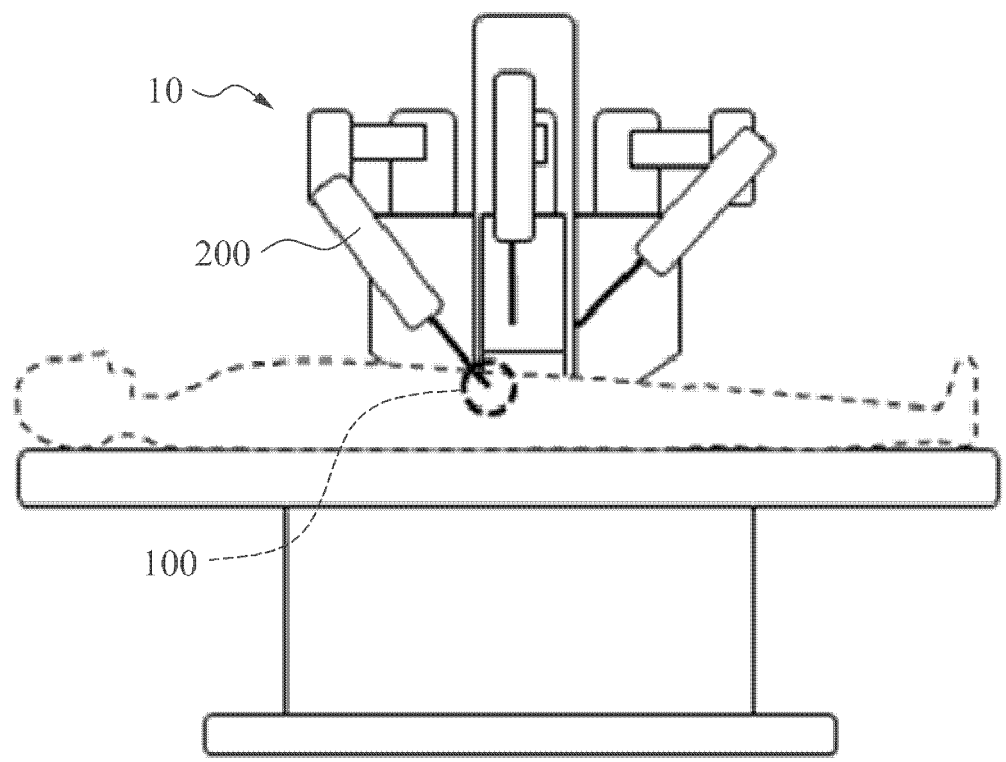
FIG. 9 illustrates a surgical robot according to an embodiment.
Figure 9:
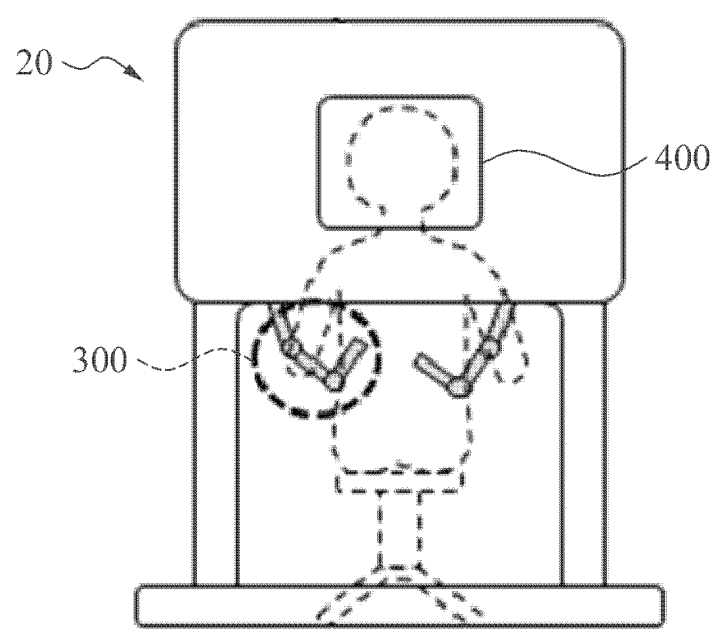

FIG. 9 illustrates a surgical robot according to an embodiment. FIG. 9 illustrates a slave robot 10 mounted with the surgical tool 100 and a master input unit 20.

As shown in FIG. 9, the surgical robot may include the master input unit 20 to generate a required signal according to a control of a controller 300, and to transmit the generated signal, and the slave robot 10 to receive the signal from the master input unit 20 and to perform an operation required for surgery of a patient. The slave robot 10 and the master input unit 20 may be integrally configured, or may be configured as separate devices and thereby be disposed separately in an operating room, although the devices need not be disposed in the same room. Communication between the master input unit 20 and slave robot 10 may be performed over a wired or wireless network, or a combination thereof, for example.

A robot arm 200 for controlling the surgery may be provided to the slave robot 10, and the surgical tool 100 may be mounted to a front end of the robot arm 200.

A display 400 may be provided to the master input unit 20. While verifying a surgery portion and an operation of the surgical tool 100 from an image of the surgical portion that is captured through an endoscope and the like, an operator may perform surgery by controlling the controller 300 of the master input unit 20. The display 400 may include a liquid crystal display (LCD) or light emitting diode (LED) display, for example. However, the disclosure is not so limited and may include other types of displays. An operator or user (e.g., a medical professional such as a physician) may remotely control the operation of the surgical robot (e.g., the arms and surgical instruments and tools attached thereto) from the master input unit 20 via the controller 300. Generally, the operator may be a physician. However, the user need not necessarily be a physician, although it would be expected that the user is a qualified or authorized operator, e.g, a medical professional. However, broadly, the operator may be any user who controls the operation of the surgical robot.

The surgical tool 100 may include at least one grasper. Each of the at least one grasper may include a pair of grips 110 that may be opened and closed based on a joint.

As described above, the grip 110 may include the support member 111, the detection member 112 provided on the support member 111 and of which the front surface contacts with a surgery portion or a surgical instrument, the biocompatible elastic material 113, and the optical fiber 114 disposed between the support member 111 and the detection member 112 to measure a force that is transferred to the detection member 112. A plurality of FBGs 1142 may be formed on the optical fiber 114 that is positioned below the detection member 112.

That is, the protruding portion 1127 which is shaped in a smoothly curved shape may be formed on the bottom surface of the detection member 112, and the concave groove portion 112 may be formed in the support member 111 to correspond to the protruding portion 1127. The FBG 1142 may be located on or adjacent to a center of the protruding portion 1127.

Due to a force transferred from the detection member 112, the FBG 1142 may receive a tensile force from a lengthwise direction and thereby may measure force that is applied to the detection member 112. Also, since a single FBG 1142 is disposed for each of the plurality of detection parts included in the detection member 112, the FBGs 1142 may measure a distribution of force by the number of detection parts included in the detection member 112.

The distribution and magnitude of force that is detected when the surgical tool 100 holds the surgical portion or the surgical instrument may be displayed on the display 400 of the master input unit 20. When the force is transferred to each of the plurality of detection parts included in the detection member 112, each of the FBGs 1142 may measure a force that is applied to a corresponding detection part. The measured distribution and magnitude of force may be visually displayed on the display 400.

Based on the distribution of force applied to the surgical tool 100 and distribution of force in each of areas of the surgical tool 100 that are displayed on the display 400, the operator may perform an elaborate surgery by operating the surgical tool 100 of the slave robot through an elaborate controlling of the controller 300.

Alternatively, the distribution and magnitude of force that is detected when the surgical tool 100 holds the surgery portion or the surgery instrument may be configured to be directly transferred to the controller 300 of the master input unit 20. When the force is transferred to each of the plurality of detection parts included in the detection member 112, each of the FBGs 1142 may measure the force that is applied to a corresponding detection part. The measured distribution and magnitude of force may be transferred to a hand of the operator through the controller 300. That is, the distribution and magnitude of force measured by each of the FBGs may be transmitted directly from the surgical tool 100 to the master input unit 20, or may be transmitted to the master input unit 20 via the slave robot 10, over a wired or wireless network, or a combination thereof.

The master input unit 20 enables a user to input an operation command to control the surgical robot and may include a user interface (UI) and display 400. Also, the master input unit 20 may include one or more devices such as foot pedals, foot switches, a small-size wrist gym ball, a joystick, a glove, a trigger gun, a voice recognition apparatus, a keyboard, a mouse and may further have additional features to assist the user in operating the surgical robot, including haptic feedback capability, head-mounted displays, or virtual reality devices, for example. As mentioned above the master input unit 20 may be remotely located from the surgical robot such that a user may input an operation command from a remote station.

Based on the distribution of force applied to the surgical tool 100 and the distribution of force in each of the areas of the surgical tool 100 that are transferred to the hand of the operator, the operator may perform an elaborate surgery by operating the surgical tool 100 of the slave robot 10 through an elaborate controlling of the controller 300.

According to the above example embodiments, a surgical robot may relieve the absence of a feeling of contact between an operator and a patient. Operators may more quickly learn how to control the surgical robot, and may perform convenient and safe surgery using the surgical surgery.

According to the above example embodiments, a surgical robot may be elaborately controlled as if the surgical robot is a hand of a human being, and may also provide a hand-touch diagnosis function.

According to the above example embodiments, a remote control robot system may include a surgical tool such as a grip. For example, the remote control robot system may include a master input unit having a controller and a slave robot to operate according to a remote control of the master input unit. The slave robot may have a robot arm with the surgical tool (e.g., a grip) which is disposed in an end portion of the robot arm.

The surgical tool may include a support member connected to the front end of the robot arm, a plurality of detection parts provided on the support member to make contact with a target object which is gripped, and an optical fiber disposed between the support member and each of the plurality of detection parts. A single FBG may be located on a rear surface of each of the plurality of detection parts. A biocompatible elastic material may be provided around the plurality of detection parts so that the plurality of detection parts may be freely movable.

A wavelength signal of light reflected from each of the FBGs may be transferred to the master input unit of the remote control robot system. Magnitude and distribution of force applied to each of the plurality of detection parts may be measured based on a change in a wavelength.

A display may be provided to the master input unit of the remote control robot system to display the distribution and the magnitude of force detected at the surgical tool. Based on visual information that is displayed on the display, the operator may further elaborately control the slave robot.

Alternatively, since the distribution and magnitude of force detected at the surgical tool may be transferred to the controller of the master input unit of the remote control robot system, the operator of the remote control robot system may further elaborately control the slave robot based on the distribution and the magnitude of force in each of areas of the surgical tool that may be transferred to a hand of the operator through the controller.

The disclosure herein has provided example embodiments of a remote control robot system including a surgical robot and a surgical tool, which may be applied, for example, in a medical setting to perform an operation on a subject (e.g., a human or animal or other lifeform). However, the disclosure is not so limited. For example, the remote control robot system including the surgical robot and the surgical tool may be used in other settings which may benefit from the surgical robot and surgical tool disclosed herein. For example, the surgical robot and surgical tool may be utilized to perform operations in any confined space or enclosure in which an operator may need to perform controlled movements using an instrument attached to a robot arm, so as to avoid or to prevent injuries to bodies or objects, that may be located or disposed within the space or enclosure, due to imprecise movements of the surgical robot. Possible settings may include, for example, mining operations, surveillance operations, inspection operations, repair operations, bomb disposal operations, etc., however again, the disclosure is not so limited.

The apparatus and methods for controlling a configuration of the remote control robot system including a surgical robot and surgical tool according to the above-described example embodiments may use one or more processors, which may include a microprocessor, central processing unit (CPU), digital signal processor (DSP), or application-specific integrated circuit (ASIC), as well as portions or combinations of these and other processing devices.

The terms "module", and "unit," as used herein, may refer to, but are not limited to, a software or hardware component or device, such as a Field Programmable Gate Array (FPGA) or Application Specific Integrated Circuit (ASIC), which performs certain tasks. A module or unit may be configured to reside on an addressable storage medium and configured to execute on one or more processors. Thus, a module or unit may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for in the components and modules/units may be combined into fewer components and modules/units or further separated into additional components and modules.

Methods for controlling a configuration of the remote control robot system including a surgical robot and surgical tool according to the above-described example embodiments may be recorded in non-transitory computer-readable media including program instructions to implement various operations embodied by a computer. The media may also include, alone or in combination with the program instructions, data files, data structures, and the like. Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules in order to perform the operations of the above-described embodiments, or vice versa. Some or all of the operations performed in methods for controlling a configuration of the remote control robot system including a surgical robot and surgical tool according to the above-described example embodiments may be performed over a wired or wireless network.

Each block of the flowchart illustrations may represent a unit, module, segment, or portion of code, which comprises one or more executable instructions for implementing the specified logical function(s). It should also be noted that in some alternative implementations, the functions noted in the blocks may occur out of the order. For example, two blocks shown in succession may in fact be executed substantially concurrently or the blocks may sometimes be executed in the reverse order, depending upon the functionality involved.

Although example embodiments have been shown and described, it would be appreciated by those skilled in the art that changes may be made to these embodiments without departing from the principles and spirit of the disclosure, the scope of which is defined by the claims and their equivalents.

What is claimed is:

1. A surgical tool, comprising:
a support member configured to be attachable to a surgical robot;
a plurality of detection parts displaceably disposed above the support member having a front surface to contact an object and a rear surface facing the support member; and
at least one detection sensor disposed between the support member and each of the plurality of detection parts to measure a force transferred to each of the plurality of detection parts, wherein
the plurality of detection parts are separated from one another to be mutually independently movable in an upward and downward direction, and
a biocompatible elastic material is provided between the respective detection parts or between each of the plurality of detection parts and the support member.

2. The surgical tool of claim 1, wherein:
the detection sensor comprises an optical fiber disposed along the rear surface of each of the plurality of detection parts, and
the optical fiber is disposed within a groove formed in the support member.

3. The surgical tool of claim 2, wherein:
the optical fiber disposed along the rear surface of each of the plurality of detection parts is provided with an optical fiber bragg grating (FBG), and when a force is transferred from each of the plurality of detection parts, the FBG receives a tensile force in a lengthwise direction to measure a force applied to each of the plurality of detection parts.

4. A surgical tool, comprising:
a support member configured to be attachable to a surgical robot;
a plurality of detection parts displaceably disposed above the support member having a front surface to contact an object and a rear surface facing the support member; and
at least one detection sensor disposed between the support member and each of the plurality of detection parts to measure a force transferred to each of the plurality of detection parts, wherein:
a convex protruding portion is formed on the rear surface of each of the plurality of detection parts, and
a concave groove portion in a shape corresponding to the protruding portion is formed in the support member.

5. The surgical tool of claim 4, wherein:
the detection sensor comprises an optical fiber disposed along the rear surface of each of the plurality of detection parts,
an optical fiber positioned on a center of a bottom surface of the protruding portion is provided with an optical fiber bragg grating (FBG), and
when a force is transferred from each of the plurality of detection parts, the FBG receives a tensile force in a lengthwise direction to measure a force applied to each of the plurality of detection parts.

6. The surgical tool of claim 5, wherein:
a single FBG is provided on the rear surface of each of the plurality of detection parts, and
a magnitude or distribution of the force applied to each of the plurality of detection parts is measured by measuring a change in a wavelength of light reflected from the FBG.

7. A surgical robot, comprising:
a master input unit having a controller;
a robot arm to operate according to a control of the master input unit; and
a surgical tool connected to an end of the robot arm to grip an object, wherein the surgical tool comprises:
a support member;
a detection member disposed above the support member having a front surface to contact the object, and a rear surface facing the support member;
at least one optical fiber disposed between the support member and the detection member to measure a force transferred to the detection member; and
a plurality of optical fiber bragg gratings (FBGs) formed on the optical fiber, wherein when a force is transferred from the detection member, each of the FBGs receives a tensile force in a lengthwise direction to measure a force applied to the detection member.

8. The surgical robot of claim 7, wherein:
the detection member is divided into a plurality of detections parts, and
each of the plurality of detection parts are separated from each other to be mutually independently movable in upward and downward directions.

9. The surgical robot of claim 8, wherein:
the plurality of detection parts are disposed along parallel rows, and
the FBGs are disposed on a plurality of optical fibers arranged in parallel.

10. The surgical robot of claim 8, wherein:
the plurality of detection parts is disposed along parallel rows, and
the FBGs are disposed on a single optical fiber arranged in a zigzagged pattern.

11. The surgical robot of claim 7, wherein:
a convex protruding portion is formed on the rear surface of the detection member,
a concave groove portion formed in the support member in a shape corresponding to the protruding portion, and
at least one FBG is disposed on a center of the protruding portion.

12. The surgical robot of claim 7, wherein:
the master input unit includes a display, and
a distribution or magnitude of the force measured by the plurality of FBGs is visually displayed on the display.

13. The surgical robot of claim 7, wherein the force measured by the plurality of FBGs is transferred by the controller of the master input unit.

14. A remote control robot system, comprising:
a master input unit having a controller; and
a slave robot to operate according to a remote control of the master input unit, the slave robot having at least one robot arm with a surgical tool disposed on an end of the robot arm,
wherein the surgical tool comprises:
a support member connected to the end of the robot arm;
a plurality of detection parts provided on the support member to contact a target object; and
an optical fiber disposed between the support member and each of the plurality of detection parts including a single optical fiber bragg grating (FBG) for each of the plurality of detection parts, and
a wavelength signal of light reflected from each of the respective FBGs is transferred to the master input unit and a magnitude or distribution of force applied to each of the plurality of detection parts is measured based on a change in a wavelength.

15. The remote control robot system of claim 14, wherein the surgical tool includes a grasper to hold an object, having a pair of grips to perform an opening and closing operation, and at least one of the grips includes the support member and the plurality of detection parts.

16. The remote control robot system of claim 14, wherein:
the optical fiber is disposed in a groove, the groove being formed in a lengthwise direction on a front side of the support member facing the detection member.

17. The remote control robot system of claim 14, wherein:
each of the plurality of detection parts includes a front side to contact the target object and a rear side facing the support member, a portion of the rear surface protruding toward the support member having a convex shape, and
the support member includes a plurality of concave groove portions, each corresponding to the convex protruding portion of the respective detection parts,
wherein each of the respective FBGs are disposed in a space between the convex protruding portion and the concave groove portion.

18. The remote control robot system of claim 17, wherein each of the respective FBG are disposed in the space at a position corresponding to a center of the convex protruding portion.

19. The remote control robot system of claim 17, wherein a biocompatible elastic material is disposed between each of the plurality of detection parts and the support member.

* * * * *